United States Patent [19]
Ramazanov et al.

[11] Patent Number: 6,117,431
[45] Date of Patent: Sep. 12, 2000

[54] **METHOD FOR OBTAINING AN EXTRACT FROM *GINKGO BILOBA* LEAVES**

[75] Inventors: Zakir Ramazanov; Maria del Mar Bernal Suarez, both of Warwick, N.Y.

[73] Assignee: Pharmline Inc., Florida, N.Y.

[21] Appl. No.: 09/454,186

[22] Filed: Dec. 3, 1999

[51] Int. Cl.$^7$ ..................................................... A01N 65/00
[52] U.S. Cl. ......................................................... 424/195.1
[58] Field of Search .......................................... 424/195.1

[56] References Cited

U.S. PATENT DOCUMENTS

| | | | |
|---|---|---|---|
| 4,466,923 | 8/1984 | Friedrich | 554/11 |
| 4,472,442 | 9/1984 | Katz | 426/427 |
| 4,482,453 | 11/1984 | Coombs et al. | 208/251 R |
| 4,490,398 | 12/1984 | Behr et al. | 426/318 |
| 4,493,854 | 1/1985 | Friedrich et al. | 426/417 |
| 4,554,170 | 11/1985 | Panzner et al. | 426/651 |
| 4,675,198 | 6/1987 | Sevenants | 426/425 |
| 4,692,280 | 9/1987 | Spinelli et al. | 554/205 |
| 4,820,537 | 4/1989 | Katz | 426/422 |
| 4,981,688 | 1/1991 | Ayroles et al. | 424/195.1 |
| 5,017,397 | 5/1991 | Nguyen et al. | 426/489 |
| 5,089,280 | 2/1992 | Ben-Nasr et al. | 426/280 |
| 5,178,735 | 1/1993 | Manabe et al. | 424/195.1 |
| 5,210,240 | 5/1993 | Peter et al. | 554/179 |
| 5,225,223 | 7/1993 | Vitzthum et al. | 426/387 |
| 5,322,688 | 6/1994 | Schwabe | 424/195.1 |
| 5,389,370 | 2/1995 | O'Reilly et al. | 424/195.1 |
| 5,399,348 | 3/1995 | Schwabe | 424/195.1 |
| 5,512,286 | 4/1996 | Schwabe | 424/195.1 |
| 5,547,673 | 8/1996 | Bombardelli | 514/783 |
| 5,637,302 | 6/1997 | Bombardelli et al. | 514/12 |
| 5,660,831 | 8/1997 | Reinhard | 424/195.1 |
| 5,700,468 | 12/1997 | Bombardelli et al. | 424/195.1 |

FOREIGN PATENT DOCUMENTS

| | | |
|---|---|---|
| 0360 556 | 5/1990 | European Pat. Off. . |
| 0477 968 | 4/1992 | European Pat. Off. . |

OTHER PUBLICATIONS

Computer Abstract Caplus 1999:137769 Liu et al "Determinatin of the flavonoids from *Ginkgo biloba* L extract by supercritical fluid chromatography" Fenxi Huaxie (1999) 27(2) 214–216.

Computer Abstract Caplus 1999:500947 Deng et al "Active components from ginkgo leaves by second supercritical fluid extraction" Zhongcaoya (1999) 30(6) 419–423.

Computer Abstract Caplus 1995:755575 Yao et al "Determination of flavonoid compounds in *Ginkgo biloba* leaves with supercritical fluid extraction and high performance" Chin. Chem. Lett. (1995) 6 (7) 589–92.

Computer Abstract Caplus 1996:436102 van Beek et al "Sample preparation of standarized extracts of *Ginkgo biloba* by supercritical fluid extraction" Phytochem Anal. (1996) 7(4) 185–191.

*Primary Examiner*—Herbert J. Lilling
*Attorney, Agent, or Firm*—Darby & Darby

[57] ABSTRACT

A novel and environmentally friendly method is disclosed for producing a purified extract from *Ginkgo biloba* leaves comprising the novel steps of differential centrifugation and extraction with supercritical $CO_2$.

18 Claims, No Drawings

METHOD FOR OBTAINING AN EXTRACT FROM GINKGO BILOBA LEAVES

FIELD OF THE INVENTION

This invention concerns a method for producing a clinically useful *Ginkgo biloba* extract that contains low levels of undesired allergenic alkyl phenols, specifically ginkgolic acid and ginkgolic acid derivatives. The method employs differential centrifugation and supercritical $CO_2$ extraction.

BACKGROUND OF THE INVENTION

Extracts from the leaves of the Maiden hair tree or *Ginkgo biloba* have long been known to possess medicinal properties. Recently, *Ginkgo biloba* extracts (GBE) have been reported for use in treating asthma, tinnitus, impotence, immunosupression and memory loss among others. However, the clinical effect of GBE that is best documented is that of a vasodilator. For this reason, GBE is used as an aid to circulation and as an enhancer of memory and cognitive function in mammals. Over the counter tablets, which are taken orally, are the most commonly available form of GBE.

The primary constituents of GBE are compounds known as flavone glycosides. Secondary components in GBE include other flavonoids, ginkgo terpene lactones (ginkgolides and bilobalide), proanthocyanidines and undesired lipophilic constituents which contain alkyl bilobalide phenols. These components are typically present in the commercial GBE products currently available. GBE products must contain at least 24% by weight of ginkgo flavone glycosides, 6% by weight of ginkgo terpene lactones, and a maximum level of ginkgolic acid of 5 ppm in order to meet the standards adopted by the German Federal Institute for Drugs and Medical Devices and by U.S. manufacturers of phytomedicines.

The alkyl phenols constituents of GBE have been reported to be responsible for phenols, GBE, allergic reactions and skin irritations suffered by individuals that ingest GBE. More specifically, 2-hydroxy-6-alkyl benzoic acids where alkyl is equal to normal $C_{13}$ to normal $C_{19}$; 2-hydroxy-6-alkenyl-benzoic acids where alkenyl is equal to normal $C_{13}$ to normal $C_{19}$ with the requisite alkenyl double bond(s) in varying positions along the alkenyl chain; and 2-hydroxy-6-alkenyl-benzoic acids where alkenyl is equal to normal $C_{13}$ to normal $C_{19}$ with the requisite triple bond(s) in various positions along the alkynyl chain; are thought to be responsible for such reactions and irritations. Representative examples of these compounds are 6-pentadecyl-2-hydroxybenzoic acid, 6-(8-pentadecenyl)-2-hydroxybenzoic acid (known as ginkgolic acid) and 6-(8-pentadecynyl)-2-hydroxybenzoic acid. In particular, high levels of these compounds (exceeding 100 ppm of the GBE) are believed to be responsible for inducing allergic contact reactions of mucous membranes such as cheilitis, stomatitis, proctitis, and pruritus ani or skin irritations such as contact dermatitis. Thus, producers of GBE have sought a method for making an economical, clinically potent GBE that has low levels of the aforementioned allergenic alkyl phenols and which therefore avoids these allergic reactions.

The main alkyl-phenol component of GBE is ginkgolic acid (2-hydroxy-6-(trans-8-pentadecenyl)benzoic acid) which possesses a normal $C_{15}$ side chain having a trans double bond at the $C_8$ position. As employed herein the term ginkgolic acid derivatives refer to any 2-hydroxy-6-alkyl, alkenyl or alkynyl benzoic acid having a carbon chain length varying from normal $C_{13}$ to normal $C_{19}$. Included in this definition of ginkgolic acid derivatives are the ginkgols which are 3-alkyl phenol derivatives.

The method of the present invention is used to produce GBE in which the amount of these compounds is reduced to less than 5 ppm. Several methods exist for removing the allergenic alkyl phenols from GBE (See, for example, U.S. Pat. No. 5,637,302 and European Patent 0 477-968). The methods for removing alkyl phenols disclosed in these patents utilize expensive, environmentally unfriendly organic solvents such as n-butanol, toluene, n-hexane, and n-heptane as extraction agents. Apart from their high cost (which is a significant drawback), these techniques are impractical for economical large scale production of GBE due to the large volume and toxicity of the solvents needed to perform the extractions.

The present invention overcomes these problems by providing an efficient and environmentally friendly process amenable to economical large scale production of pharmaceutical grade GBE that is essentially free of ginkgolic acid and ginkgolic acid derivatives.

The present invention employs a supercritical fluid extraction step. As used herein, the term supercritical fluid means a gas existing above its critical temperature and pressure as defined in its phase diagram. When a gas such as $CO_2$ is compressed, above its critical temperature, its density greatly increases, so the gas has the density of a liquid and the diffusivity of a gas. This makes supreciritical fluids superior solvents. The solvent properties of supercritical $CO_2$ can be attenuated by changing the pressure at which the extraction is performed. Typical ranges of temperature and pressure for supercritical $CO_2$ extractions which are useful in the present invention are between about −10 and about 180° C. and between about 100 and about 350 atm (see, for example, U.S. Pat. No. 4,466,923).

SUMMARY OF THE INVENTION

The present invention is an environmentally friendly method for making a clinically useful GBE extract containing less than 5 ppm ginkgolic acid and ginkgolic acid derivatives. In practicing the method, *Ginkgo biloba* leaves are mixed with a water miscible $C_{1-4}$ alcohol:water mixture to form a suspension. The suspension is treated to remove particulates and form a GBE solution. The GBE solution is thereafter concentrated to remove alcohol, diluted with water, and subjected to differential centrifugation to remove solids. The centrifuged solids free solution is dried, and the resulting solid is extracted with supercritical $CO_2$.

OBJECTS OF THE INVENTION

It is an object of the invention to provide an environmentally friendly and economical method for producing *Ginkgo biloba* extract which contains less than 5 ppm ginkgolic acid and ginkgolic acid derivatives.

Another object of the invention is a method to make a GBE using differential centrifugation.

A further object of the invention is a method to make a GBE using supercritical $CO_2$ extraction.

A further object of the invention is to make GBE containing at least 24% by weight of flavone glycosides and at least 6% by weight of ginkgo terpene lactones and a maximum of 5 ppm ginkgolic acid and ginkgolic acid derivatives.

A still further object of the invention is to make a GBE suitable for use in the preparation of pharmaceutical formulas, soft-drink beverages, infusion, tablets or capsules.

These and other objects of the present invention will be more readily appreciated and understood from a consideration of the following detailed description.

DETAILED DESCRIPTION OF THE INVENTION

The present invention is an environmentally friendly and economical method for producing a GBE containing less than 5 ppm by weight of allergenic ginkgolic acid and ginkgolic acid derivatives.

According to the invention, a clinically useful GBE extract containing not more than 5 ppm total by weight of ginkgolic acid and ginkgolic acid derivatives is produced by extracting *Ginkgo biloba* leaves with a mixture of a water miscible alcohol and water. The preferred mixture is 70:30 (v/v) (volume/volume) (ethanol/water) although methanol, butanol and propanol are also useful in practicing the invention. The *Ginkgo biloba* leaves are preferably dried prior to the extraction and contain not more than 6% by weight of water. The dried leaves are preferably extracted in the form of finely divided particles having an average particle size of between about 4 and about 10 mm. In the preferred embodiment, a particle size of about 4 mm is employed. The extraction may be carried out at a temperature of between about 25° C. and about 85° C. and preferably at 60° C. The extraction is preferably carried out by mixing or agitating the constituents for between 1 and 24 hours and preferably for about 12 hours.

After the extraction has been completed, particulates are removed by passing the resulting suspension through a centrifuge (ALFA Laval model CHPX supplier supplemented with a disk-stack centrifuge, Alfa Laval S A Spain Antonio de Cabezón; 27; ES-28034 Madrid), or alternately filtered (vacuum filtration through filter paper) at room temperature (20° C.).

The resulting solution is then concentrated by distillation under reduced pressure (100 mm Hg) to remove alcohol. The concentration is continued until the suspension has a solids content of between about 20% and 30% by weight as determined by a hydrometer (Fisher Scientific). Water is then added to the suspension until a solids content of between about 5% and 10% by weight, as determined by a hydrometer (Fisher Scientific) is achieved. At this point in the procedure, the suspension typically contains more than 10,000 ppm by weight ginkgolic acid and ginkgolic acid derivatives.

The suspension containing these high levels of ginkgolic acid and ginkgolic acid derivatives is then subjected to differential centrifugation (using e.g., a Westfalia separator model C300 available from Westfalia, Separator, Deutschland GmbH, Werner-Habig-Str. 1 59302, Oelde, Germany) at a temperature of between about 5° C. and about 25° C., and preferably 5° C. The differential centrifugation begins at an initial speed of about 200 rpm and is increased in increments of 500 rpm to about 5,000 rpm over a period of about between 1 and 3 hours, and preferably over a 2-hour period. The initial speed is raised in increments of 500 rpm at approximately 10-minute intervals. At the end of each 10-minute interval, the debris (particulate material) is removed from the centrifuging tube. Utilizing a Westfalia Separator C300 centrifuge, extract can be continuously added to the separator and centrifuged while simultaneously removing solids (i.e., continuous flow regime).

The resulting solution is then spray dried utilizing a spray dryer model VRA-1 (Spray Drier, Model VRA-1 manufactured by Vzduchotecnika, Novo mesto-city, Slovak Republic). Spray drying is the most widely used industrial process involving particle formation and drying. The dryer consists of feed pump, atomizer, air heater, air disperser, drying chamber, and systems for exhaust air cleaning and powder recovery. It is highly suited for the continuous production of dry solids in powder form from liquid extract. In the spray drying process, the liquid containing the dissolved or suspended solid is sprayed into a hot gas, (e.g., hot air or nitrogen) converting the liquid into a free flowing particulate solid. The solid typically contains more than 5,000 ppm ginkgolic acid and ginkgolic acid derivatives. This solid material is then extracted with supercritical $CO_2$ at a pressure of between about 50 atm and about 350 atm and preferably at 200 aAtm. The supercritical $CO_2$ extraction is carried out at a temperature of between about $-10°$ C. and about 180° C. and preferably between 150° C. and 155° C. for between 1 and about 3 hours and preferably for 2 hours. The golden yellow solid remaining after the initial supercritical $CO_2$ extraction typically contains more than 20 ppm of ginkgolic acid and ginkgolic acid derivatives. To further reduce the level of ginkgolic acid ginkgolic acid derivatives, the solid is extracted a second time with supercritical $CO_2$ at a pressure of between about 50 atm and about 350 atm and preferably at about 200 atm. The supercritical $CO_2$ extraction is carried out at a temperature of between about $-10°$ C. and about 180° C. and preferably at a temperature of between 150 and 155° C. for between about 1 and about 3 hours and preferably for two hours. The resulting GBE, a golden yellow powder, has less than 5 ppm of ginkgolic acid and ginkgolic acid derivatives.

The invention is further illustrated in the following example.

EXAMPLE 1

A. Alcohol/Water Extraction

Dried *Ginkgo biloba* leaves (less than 6% by weight of water) are milled using a jet mill to an average particle size of 4 mm. To the particles is added about a 10-fold excess by weight of a 70:30 v/v (volume/volume) mixture of ethyl alcohol:water, respectively. The resultant suspension of *Ginkgo biloba* leaves is then agitated at 60° C. for 12 hours. The suspension is centrifuged in a Westfalia separator model C300 by passing the crude extract through the centrifuge to remove particulate matter. The particulate free solution is then concentrated by distillation at a reduced pressure (100 mm Hg at 65–70° C.) to remove ethyl alcohol. The distillation is continued until the resulting suspension contains between about 20 to 30% by weight of solids determined using a hydrometer (Fisher Scientific). The solids content of the suspension is reduced to between about 5 to 10% by the addition of water as determined using a hydrometer (Fisher Scientific).

B. Differential Centrifugation

The suspension from A above is subjected to continuous flow differential centrifugation. Utilizing a Westfalia Separator C300 at a starting speed of 200 rpm and a temperature of 5° C., the rotation speed is increased slowly, in increments of 500 rpm every 10 minutes, with removal of solids at the end of each interval, until a speed of 2,000 rpm was attained. The centrifuge was then held at 2,000 rpm for 10 minutes after which time solids were removed. The speed was then increased to 2,500 rpm and held at this speed for 10 minutes after which time solids were removed. The speed was then increased to 3,500 rpm and held at this speed for 10 minutes after which time solids were removed. The speed was then raised to 5,000 rpm and held for 10 minutes after which time solids were removed. The temperature of the suspension is held constant at 5° C. throughout the differential centrifugation procedure. After removal of the solids, a clear yellow aqueous solution of GBE remains.

C. Spray Drying of GBE Solution

The GBE solution of step B is spray dried utilizing conventional hot air spray dryer (Model VRA1 available from Vzduchotorg Ltd., Trencianska 17, 91501 Nóvo Mesto Nad Vahom, Slovak Republic). The spray drying process of liquid GBE was started by pumping the solution through the atomizer forming liquid droplets in the drying chamber where the droplets contacted the hot air. The liquid drops of GBE solution were produced by passing liquid through nozzle atomizers. Evaporation of moisture from the droplets and formation of dry particles proceed under controlled temperature: 170° C. on inlet (top of spray drier) and 85° C. at the outlet (bottom of spray drier). Powdered GBE is precipitated to the bottom of spray drier and discharged continuously from the drying chamber.

D. Extraction with Supercritical $CO_2$

Utilizing a Model T-01 (available from Kobe Steel, Ltd., Kabushiki Kaisha Kobe Seikosho, Kobe, Japan) supercritical fluid extractor supplemented with an extractor Model T-1 Supercritical Fluid Extractor (available from Kobe Steel, Ltd.), receiver Model V-01 and V-02 (available from Kobe Steel, Ltd.), pump and heat exchangers Model P-01 High Pressure Pump (available from Kobe Steel, Ltd.), the solid GBE from step C is charged into the extractor and then supercritical $CO_2$ is fed into the separator at a pressure of 200 atm and at a temperature of between 150 and 150° C. via a high pressure pump. The amount of $CO_2$ added is in a 5-fold weight excess to the solid GBE from step C. The extraction is carried out for two hours. Lipophillic compounds (including ginkgolic acid and ginkgolic acid derivatives) are dissolved in the liquid $CO_2$. The supercritical solution is removed from the extractor via the pressure reduction valve. The gas is then vented from the extractor and the solid GBE extract collected. The supercritical extraction process is then repeated a second time using the solid GBE recovered from the initial supercritical extraction step.

The material obtained after the repeated supercritical $CO_2$ extraction is a GBE containing at 24% by weight of flavone glycosides and 6% by weight of ginkgo terpene lactones and less than ppm (total) of ginkgolic acid and ginkgolic acid derivatives.

We claim:

1. A method of preparing a *Ginkgo biloba* extract comprising the steps of
   (i) extracting *Ginkgo biloba* leaves with an alcohol/water solution;
   (ii) removing particulate materials from said solution;
   (iii) removing alcohol from said solution to form an aqueous suspension;
   (iv) subjecting said aqueous suspension to differential centrifugation to form a second solution;
   (v) drying the second solution to form a solid; and
   (vi) extracting said solid with supercritical $CO_2$ to yield said *Ginkgo biloba* extract, said extract product containing less than 5 ppm in total of ginkgolic acid and ginkgolic acid derivatives.

2. The method according to claim 1 which comprises drying said *Ginkgo biloba* leaves prior to said mixing step.

3. The method according to claim 2 which comprises milling *Ginkgo biloba* leaves prior to said mixing step.

4. The method according to claim 1 wherein said alcohol is a water miscible $C_{1-4}$ alcohol.

5. The method according to claim 4 wherein said alcohol is ethyl alcohol.

6. The method according to claim 1 wherein said ratio of said alcohol/water mixture is 70 alcohol:30 water by volume.

7. The method according to claim 1 which comprises holding said aqueous suspension at a temperature of about between 5° C. and 25° C. during said differential centrifugation step.

8. The method according to claim 1 which comprises carrying out said differential centrifugation for between about 1 to 3 h.

9. The method according to claim 8 which comprises carrying out said differential centrifugation for 2 hours at 5° C.

10. The method according to claim 1 which comprises extracting said solid with supercritical $CO_2$ at a pressure of between about 50–350 atm.

11. The method according to claim 10 wherein said pressure is 200 atm.

12. The method according to claim 1 which comprises extracting said solid with supercritical $CO_2$ at a temperature of about between 10–180° C.

13. The method according to claim 12 wherein said temperature is between 150–155° C.

14. The method according to claim 1 which comprises extracting said solid with supercritical $CO_2$ for between about 1 to 3 h.

15. The method according to claim 14 which comprises conducting said extraction for 2 h.

16. The method according to claim 1 wherein the weight ratio of said solid to said supercritical $CO_2$ is about 1:5.

17. The method according to claim 1 which comprises agitating said *Ginkgo biloba* leaves and alcohol/water mixture.

18. The method according to claim 1 which comprises conducting said differential centrifugation at an initial speed of about 200 rpm and incrementally increasing said speed over a period of between about 1 and 3 h to about 5,000 rpm.

* * * * *